United States Patent [19]

Hollister

[11] Patent Number: 4,621,120

[45] Date of Patent: Nov. 4, 1986

[54] POLYMERIC ANTIBACTERIAL COMPOSITIONS

[75] Inventor: Kenneth R. Hollister, Pittsford, N.Y.

[73] Assignee: Eastman Kodak Company, Rochester, N.Y.

[21] Appl. No.: 718,303

[22] Filed: Apr. 1, 1985

[51] Int. Cl.$^4$ .................. C08F 114/02; C08F 214/02; A01N 33/12

[52] U.S. Cl. .............................. 525/327.1; 525/328.2; 525/329.4; 525/331.4; 525/333.3; 525/379; 525/916; 524/555; 424/25; 424/49; 424/54; 424/78; 514/642; 514/643

[58] Field of Search ....................... 424/78, 49, 54, 28; 514/642, 643; 525/380, 326.6, 326.7, 327.1, 328.2, 329.4, 331.4, 333.3, 379, 381, 916, 393; 524/555

[56] References Cited

U.S. PATENT DOCUMENTS

| | | | |
|---|---|---|---|
| 3,170,901 | 2/1965 | Melamed et al. | 526/292.95 |
| 3,984,537 | 10/1976 | Harrison et al. | 424/54 |
| 4,025,617 | 5/1977 | Green et al. | 514/213 |
| 4,161,518 | 7/1979 | Wen et al. | 424/52 |
| 4,166,846 | 9/1979 | Shigematsu et al. | 424/81 |
| 4,193,800 | 3/1980 | Iwama et al. | 430/213 |
| 4,323,551 | 4/1982 | Parran, Jr. | 424/54 |
| 4,370,314 | 1/1983 | Gaffar | 424/54 |
| 4,374,124 | 2/1983 | Jarcho | 424/54 |
| 4,482,680 | 11/1984 | Sheldon et al. | 525/331.4 |

OTHER PUBLICATIONS

"New Polymeric Biocides: Synthesis & Antibacterial Activities of Polycations with Pendant Biguanide Groups", Antimicrobial Agents and Chemotherapy, Aug. 1984, pp. 139–144, vol. 26, No. 2.

"Agent for the Removal & for Hindering the Formation of Dental Plaque", Chem. Abst., vol. 90, 1979, p. 376, 90:127539w.

"A Comparison Between Chlorhexidine & Some Quaternary Ammonium Compounds with Regard to Retention, Salivary Concentration & Plaque-Inhibiting Effect in Human Mouth After Mouth Rinses", Chem. Abst., vol. 90, 1979, p. 32, 90:66822j.

Primary Examiner—Morton Foelak
Assistant Examiner—Nathan M. Nutter
Attorney, Agent, or Firm—John R. Everett

[57] ABSTRACT

Polymers having antibacterial activity are disclosed. The polymers are water-dispersible vinyl copolymers comprising (a) from 15 to 90 mole percent of recurring polymerized vinyl monomer units having a quaternary nitrogen cationic group containing an alkyl substituent having 14 to 20 carbon atoms and (b) from 10 to 85 mole percent recurring polymerized vinyl monomer units having a quaternary nitrogen cationic group having one or more alkyl substituents containing less than 14 carbon atoms.

16 Claims, No Drawings

POLYMERIC ANTIBACTERIAL COMPOSITIONS

FIELD OF THE INVENTION

This invention relates to vinyl copolymers having antibacterial activity and to antibacterial compositions comprising such copolymers.

BACKGROUND OF THE INVENTION

Cationic antibacterial compounds are known.

U.S. Pat. No. 4,370,314 discloses antibacterial quaternary ammonium compounds in which one of two of the substituents on the quaternary nitrogen has a chain length of 8 to 20 carbon atoms. The remaining substituents have a lower number of carbon atoms, typically alkyl or benzyl groups of 1 to 7 carbon atoms. The compounds are useful in dental compositions because of their specific antiplaque activity. Examples include dodecyltrimethylammonium bromide, benzyldimethylstearylammonium chloride, cetylpyridinium chloride and quaternized 5-amino-1,3-bis(2-ethylhexyl)-5-methyl hexahydropyrimidine.

U.S. Pat. No. 4,370,314 broadly suggests that polymeric cationic quaternary antibacterial agents are also useful. However, no specific polymer examples are disclosed. Experimental evidence has shown that many polymerized cationic quaternary compounds are ineffective as antibacterial agents or less effective than the monomers from which they are derived. Many of the polymers are not water-dispersible. That is they are either insoluble or incapable of forming stable suspensions in aqueous media. Good coating coverage of the polymers onto substrates such as human teeth cannot be obtained. Without good coatings, the antibacterial activity of such polymers will be spotty.

SUMMARY OF THE INVENTION

The present invention provides a water-dispersible vinyl copolymer comprising (a) from 15 to 90 mole percent of recurring polymerized vinyl monomer units having a quaternary nitrogen cationic group containing an alkyl substituent having 14 to 20 carbon atoms and (b) from 10 to 85 mole percent recurring polymerized vinyl monomer units having a quaternary nitrogen cationic group having one or more alkyl substituents containing less than 14 carbon atoms.

The water-dispersible vinyl polymers of this invention have antibacterial activity, particularly against bacteria involved in tooth decay and plaque accumulation on human teeth. The polymers have enhanced adherence to a powdered surface having the composition of human tooth enamel compared to similarly structured non-polymeric compounds. This means that the polymers are likely to be more effective as antibacterial agents compared to such non-polymeric compounds. Moreover, it is expected that aqueous compositions of such polymers would have application as antibacterial agents in cuts, burns and as disinfectants and the like.

DESCRIPTION OF THE PREFERRED EMBODIMENTS

In a preferred embodiment, the vinyl polymers have the structure

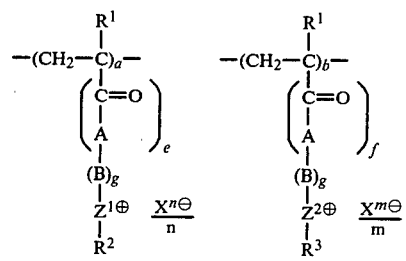

wherein
each $R^1$ is independently hydrogen or methyl;
each A is independently —O— or —NH—;
each B is independently alkylene of about 1 to 20 carbon atoms, arylene of about 6 to 14 carbon atoms and arylenealkylene of about 7 to 15 carbon atoms;
$Z^1$ and $Z^2$ are each independently a quaternary nitrogen containing group having the structure

or a quaternary nitrogen containing group having the structure

wherein
G represents the carbon, hydrogen and hetero atoms necessary to complete a substituted or unsubstituted mono- or polycyclic nitrogen-containing cationic group having about 5 to 14 ring carbon and hetero atoms; or $Z^2$ taken together with $R^3$ represents a monovalent group having the structure

wherein G is as defined above;
$R^2$ is an alkyl group having 14 to 20 carbon atoms;
$R^3$, $R^4$ and $R^5$ are each independently an alkyl group of 1 to 4 carbon atoms;
$X^n/n$ and $X^m/m$ are independently mono- or multivalent acid anions in which n is 1 to 3 and m is 1 to 3;
a is 15 to 90 mole percent;
b is 10 to 85 mole percent; and
e, f, g and h are each independently 0 or 1.

Water-dispersable, as used herein, means that the vinyl polymers are either water-soluble or can be suspended in aqueous medium without settling out.

Alkylene refers to substituents such as methylene, ethylene, trimethylene, propylene, octadecylene, and the like. Arylene refers to substituents such as phenylene and naphthylene. Arylenealkylene refers to substituents such as phenylenemethylene and phenyleneethylene.

Alkyl refers to methy, ethyl and butyl, etc. Examples of quaternary nitrogen atom-containing cationic heterocyclic groups include pyridinium, imidazolium, piperazinium, morpholinium, etc.

Useful monovalent anions include halides such as $F^-$, $Br^-$, $Cl^-$, $I^-$, p-toluenesulfonate ($PTS^-$), $NO_3^-$, $CH_3COO^-$ and $BF_4^-$. Useful monovalents anions include $SO_4^{-2}$, $PO_4^{-3}$, $SO_3^{-2}$ and $CO_3^{-2}$.

It is necessary to have at least 15 mole percent of the recurring unit containing the 14 to 20 carbon alkyl substituted quaternary nitrogen for effective antiplaque activity. Amounts up to 90 mole percent are useful. Above 90 mole percent the polymer may not be water-dispersible.

It is necessary to have at least 10 mole percent of the less than 14 carbon atom alkyl substituted quaternary nitrogen to render the polymer water-soluble or water-dispersible while simultanously contributing to the antiplaque activity. Amounts up to 85 mole percent are effective. Above 85 mole percent the antiplaque activity is diminished to unsatisfactory levels.

One procedure for making the water-dispersible polymers of this invention is schematically presented below. The method in general involves solution polymerization followed by sequential reaction of the resulting solution polymer with at least two different amines.

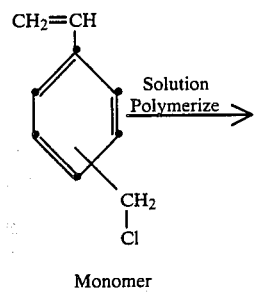

Monomer

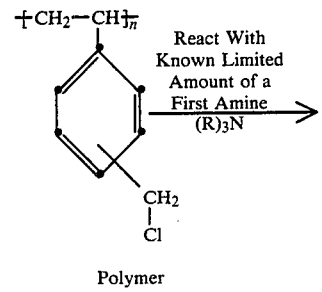

Polymer

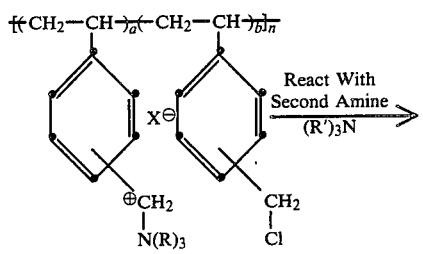

Solution Polymer

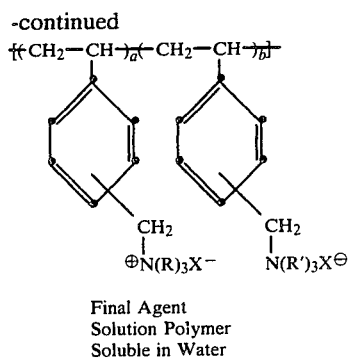

Final Agent
Solution Polymer
Soluble in Water

The water-dispersible polymers of this invention may also include from 0 to 50 mole percent of other recurring units for the purpose of controlling physical and chemical properties of the polymers such as solubility, adhesion, glass transition temperature, etc. Examples of such recurring units include polymerized monomers such as styrene and substituted styrenes exemplified by chloromethylstyrene and vinylbenzyl alcohol; acrylic monomers including an acrylic acid, acrylic acid esters; acrylic acid amides exemplified by ethyl acrylate, 2-ethylhexyl methacrylate, acrylamide, methacrylamide and N-isopropylacrylamide; vinyl ethers such as methyl vinyl ether.

The water-dispersible polymers can also include from 0 to 10 mole percent of recurring crosslinkable groups. Such recurring units are included in some cases to influence the particle size and dispersability of the polymers of this invention. Useful recurring units include polymerized divinylbenzene, ethylene diacrylate, ethylene dimethacrylate, N,N'-methylenebisacrylamide, etc.

When other recurring monomer units are included in the copolymer to control physical or chemical properties or to include crosslinking groups, the following is a schematic approach for making the water-dispersible vinyl copolymers of this invention. In general the reaction involves latex polymerization followed by sequential quaternization reactions with two different amines.

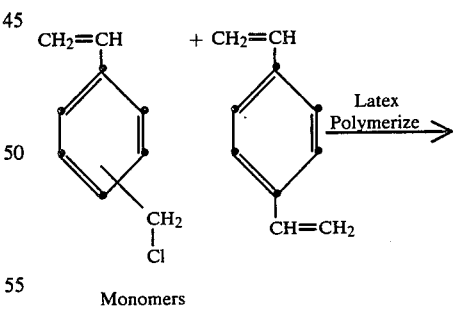

Monomers

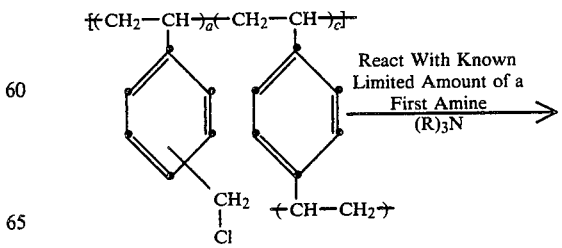

Crosslinked Latex Polymer

-continued

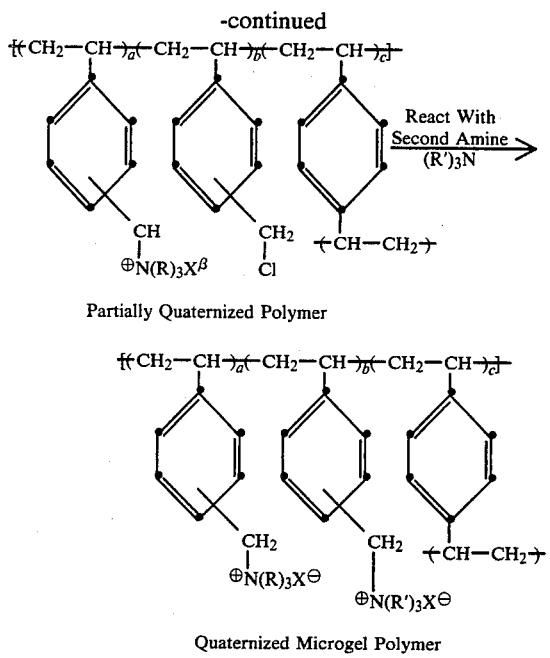

Partially Quaternized Polymer

Quaternized Microgel Polymer

Microgels are dispersions of insoluble crosslinked polymers in a liquid medium which normally (uncrosslinked) are soluble in that medium. They are highly swollen by the medium in which they are dispersed. See V. E. Shashoua & R. G. Beamon, "Microgel: An Idealized Polymer Molecule", *J. Pol.Sc.*, Vol. XXXIII, pp. 101–117 (1958).

Alternatively, the individual quaternary ammonium salt monomers can be prepared by the quaternization techniques shown. The resulting monomer salts can then be polymerized in the desired ratios by conventional polymerization techniques, with or without additional monomers.

The following examples are presented to further illustrate the foregoing schematic methods of making the water-dispersible vinyl copolymer of this invention.

EXAMPLE 1

Poly[N-(m-+p-vinylbenzyl)-N,N-dimethyl-N-octadecylammonium chloride (60:40) -co-N-(m-+p-vinylbenzyl)-N,N,N-trimethylammonium chloride (60:40)](mole ratio 1:1.5)

A. Synthesis of poly[m- +p-Chloromethylstyrene (60:40)]

A round-bottom flask fitted with a stirrer, a reflux condenser and a liquid addition system comprised of a reservoir connected to the flask through a metering pump, was immersed in a 60° C. bath and charged with 2400 ml of $N_2$-sparged water and 192 ml of a 5.6% aqueous solution of poly(sodium methacrylate). The reservoir was charged with a solution of 16.80 gm of benzoyl peroxide in 800.0 gm of m-+p-chloromethylstyrene (60:40). The contents of the reservoir were pumped into the stirring reaction mixture over 138 minutes following which the reaction mixture was stirred at 60° C. overnight. Upon cooling, the reaction mixture was centrifuged and the liquid decanted from the precipitate. The precipitate was washed and centrifuged three times in methanol and then dried. A total of 771.1 gm of fine white beads was obtained.

B. Quaternization

A flask fitted with a stirrer, a reflux condenser and an addition funnel was immersed in an 80° C. bath and charged with 22.89 gm (0.15 molar equivalent) of the above homopolymer and 206 ml of 2-methoxyethanol. The addition funnel was charged with 21.28 gm of a 25% solution of trimethylamine in methanol (0.090 mole). After stirring the reaction mixture for 15 minutes, the contents of the addition funnel were added over 1 minute. The reaction mixture was stirred an additional hour following which a solution of 17.85 gm (0.060 mole) of N,N-dimethyloctadecylamine in 54 gm of methanol was added over 15 minutes. Subsequently, the reaction mixture was stirred at 80° C. overnight and then cooled. Small scale tests confirmed that the product is soluble in water.

C. Ion Exchange and Purification

The polymer dope from above was diluted to 700 ml with distilled water and diafiltered in a small diafiltration apparatus. During the initial two hours of diafiltration, 1667 gm of a 10% solution of ammonium fluoride in water was added to the distilled water feed stream. Diafiltration was continued using only distilled water in the feed stream until the output flux gave a negative silver nitrate test for halogen. The retained polymer solution was then removed from the apparatus. It comprised 1271 gm and contained 1.9% solids. A small sample was freeze dried for analysis. Analysis calculated for $C_{94}H_{158}F_5N_5$: 77.7% C, 11.0% H, 6.5% F, 4.8% N. Found: 76.5% C, 10.8% H, 4.6% F, 3.9% N. Inherent viscosity in 1M aqueous sodium chloride is 0.1.

EXAMPLE 2

Poly[N-(m-+p-vinylbenzyl)-N,N-dimethyl-N-hexadecylammonium chloride (60:40) -co-N-(m-+p-vinylbenzyl)-N,N,N-trimethylammonium chloride (60:40) -co-p-divinylbenzene](molar ratio 87.75:9.75:2.5)

A. Synthesis of poly[m-+p-chloromethylstyrene (60:40) -co-p-divinylbenzene](molar ratio 97.5:2.5)

A round-bottom flask fitted with a stirrer, a reflux condenser and an addition funnel was immersed in a 65° C. bath and charged with 9.34 gm of a 50% aqueous solution of Surfactant 10G (Olin), 2.34 gm of cetyltrimethylammonium bromide and 970 ml of distilled water. A separate flask was charged with 457.86 gm of m-+p-chloromethylstyrene (60:40), 18.21 gm of p-divinylbenzene (55% active), 9.34 gm of a 50% aqueous solution of Surfactant 10G (Olin), 2.34 gm of cetyltrimethylammonium bromide, 0.93 gm of 2,2'-azobis(2-amidinopropane) hydrochloride and 420 ml of distilled water. This mixture was stirred rapidly for a few minutes to form an emulsion and was then transferred to the addition funnel attached to the reaction vessel. At this point, 8.40 gm of 2,2'-azobis(2-amidinopropane) hydrochloride was added to the reaction vessel following which the contents of the addition funnel were added at constant rate over 60 minutes with continuous stirring under nitrogen. At this point, an additional 0.092 gm of 2,2'-azobis(2-amidinopropane) hydrochloride was added and the system stirred an additional 3 hours at 65° C. The reaction mixture was then diluted with 1869 ml of distilled water, cooled to room temperature and filtered through a milk filter. The filtrate was a milky white latex which comprised 8890 gm and contained 10.6% solids.

B. Quaternization and Purification

A flask fitted with a stirrer, a reflux condenser and an addition funnel was charged with 100 gm of the above latex after adjusting its pH to 7.1 with 14.5 ml of 0.1 N sodium hydroxide. The flask was immersed in a 60° C. bath and the reaction mixture stirred under $N_2$ as 1.60 gm of a 25% solution of trimethylamine in methanol was added quickly from the addition funnel. After stirring at 60° C. for 20 minutes, a solution of 16.49 gm of N,N-dimethyl-N-hexadecylamine in 50 gm of isopropyl alcohol was added over 2 minutes. After stirring at 60° C. for 30 minutes, 100 ml of distilled water was added and the system stirred another 4 hours. The dispersion which resulted was treated with 11.16 gm of anhydrous sodium acetate dissolved in 45 ml of distilled water and stirred another 20 minutes at 60° C. It was then cooled to room temperature and diafiltered with distilled water for ten turnovers. The resulting latex was readily filtered through a glass filter with a nominal 2.7 micrometer pore size leaving very little residue. The resulting latex comprised 987.5 gm and contained 1.6% solids. A small sample was freeze-dried for analysis. Elemental analysis calculated for $C_{10947}H_{19054}N_{390}Cl_{390}$: 77.0% C, 11.5% H, 3.3% N, 8.3% Cl. Found: 73.4% C, 11.1% H, 3.0% N, 5.5% Cl.

EXAMPLE 3

Poly[N-(m-+p-vinylbenzyl)-N,N-dimethyl-N-octadecylammonium chloride (60:40) -co-N-(m-+p-vinylbenzyl)-N,N,N-trimethylammonium chloride (60:40) -co-N-(m-+p-vinylbenzyl 9-anthrylmethyl ether (60:40)](mole ratio 59:40:1)

A. Synthesis of Poly[m-+p-chloromethylstyrene (60:40) -co-N-(m-+p-vinylbenzyl) 9-anthrylmethyl ether (60:40)](mole ratio 99:1)

A solution of 60.49 gm of m-+p-chloromethylstyrene (60:40) and 1.30 gm of m-+p-vinylbenzyl 9-anthrylmethyl ether (60:40) in 92 ml of N,N-dimethylformamide was sparged with $N_2$ for 40 minutes, treated with 0.3087 gm of 2,2'-azobis(2methylpropionitrile) and stirred overnight at 60° C. under $N_2$. At this point an additional 0.3087 gm of 2,2'-azobis(2-methylpropionitrile) was added and the reaction mixture stirred an additional five days at 60° C. under $N_2$. The resulting viscous pale yellow solution was diluted to 20% solids with N,N-dimethylformamide following which the polymeric product was precipitated and washed in excess isopropyl alcohol using a blender. An off-white powder resulted which after drying under $N_2$/vacuum at room temperature was found to comprise 50.35 gm. Analysis calculated for $C_{915}H_{911}Cl_{99}O$: 71.2% C, 6.0% H, 22.7% Cl. Found: 70.4% C, 6.4% H, 20.7% Cl.

B. Quaternization

A solution of 15.59 gm of the above polymer in 140 ml of 2-methoxyethanol was stirred under $N_2$ at 80° C. as 14.19 gm of a 25% solution of trimethylamine in methanol was added over 1 minute. After stirring at 80° C. for an hour, the reaction mixture was treated with 11.90 gm of N,N-dimethyl-N-octadecylamine dissolved in 36 ml of methanol over a period of 20 minutes. The reaction mixture was stirred under $N_2$ at 80° C. overnight. A clear, pale yellow solution resulted which was diluted to 1 liter with distilled water. Upon purifying the resulting solution by diafiltration, it was found to comprise 808.4 gm of a clear solution which contained 2.8% solids. By fluorescence measurement compared to a reference standard using an excitation wavelength of 370 nm and measuring emission at 425 nm, the composition was found to contain 1.0 mole percent of units derived from m-+p-vinylbenzyl 9-anthrylmethyl ether.

Additional useful water-dispersable vinyl polymers are presented in Table I.

TABLE I

| Polymer | |
|---|---|
| 1 | Poly[N—(m- + p-vinylbenzyl)-N,N—dimethyl-N—octadecylammonium chloride (60:40) -co-N—(m- + p-vinylbenzyl)-N,N,N—trimethylammonium chloride (60:40)] (mole ratio 1:1.5) $\{\eta\}$ = 0.25 in DMF.* |
| 2 | Poly[N—(m- + p-vinylbenzyl)-N,N—dimethyl-N—hexadecylammonium chloride (60:40) -co-N—(m- + p-vinylbenzyl)-N,N,N—trimethylammonium chloride (60:40) -co-p-divinylbenzene] (molar ratio 87.75:9.75:2.5) |
| 3 | Poly[N—(m- + p-vinylbenzyl)-N,N—dimethyl-N—octadecylammonium chloride (60:40) -co-N—(m- + p-vinylbenzyl)-N,N,N—trimethylammonium chloride (60:40) -co-m- + p-vinylbenzyl 9-anthrylmethyl ether (60:40)] (mole ratio 59:40:1) |
| 4 | Poly[N,N—dimethyl-N—(3-methacrylamidopropyl)-N—octadecylammonium chloride-co-N—(3-methacrylamidopropyl)-N,N,N—trimethylammonium chloride] (mole ratio 1.0:1.5) $\{\eta\}$ = 1.42 methanol.* |
| 5 | Poly(N—methyl-4-vinylpyridinium chloride-co-N—octadecyl-4-vinylpyridinium chloride) (mole ratio 2.0:1.0) $\{\eta\}$ = 0.62 in methanol.* |
| 6 | Poly[N—(m- + p-vinylbenzyl)-N,N—dimethyl-N—octadecylammonium chloride (60:40) -co-N—(m- + p-vinylbenzyl)-N,N,N—trimethylammonium chloride (60:40)] (mole ratio 1:2.85) $\{\eta\}$ = 0.45 in 1.0 M NaCl solution. |
| 7 | Poly[N—(m- + p-vinylbenzyl)-N,N—dimethyl-N—octadecylammonium chloride (60:40) -co-N—(m- + p-vinylbenzyl)-pyridinium chloride (60:40) -co-N—(m- + p-vinylbenzyl)-N N,N—trimethylammonium chloride (60:40)] (mole ratio 1.0:2.0:0.85) $\{\eta\}$ = 0.30 in DMF.* |

*The inherent viscosity $\{\eta\}$ given are for the unquaternized prepolymers measured at a concentration of 0.25 g/dl at 25° C. in the solvent indicated (DMF = N,N—dimethylformamide) except for Example 6 wherein $\{\eta\}$ is given for the final quaternized polymer.

The concentration of water-dispersable polymers in aqueous solution or aqueous dispersion of the invention which have effective antibacterial action is between 0.001 and 10 weight percent. Concentrations below these ranges are only marginally effective, although for some uses it is conceivable that these low concentrations will be effective particularly against extremely low concentrations of bacteria. Amounts above this range will be effective but seem to provide no added benefit in terms of increased antibacterial activity.

The water-dispersible polymers of this invention are used to make antibacterial compositions. In one embodiment the antibacterial composition may be substantially liquid in character, such as a mouthwash. In such a preparation the vehicle is generally a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70 percent to about 99.9 percent by weight of the preparation. The pH of such liquid preparations is generally in the range of from about 7 to about 9.5 and typically from about 7.0 to 8.7.

In certain other embodiments of this invention, the antibacterial composition may be substantially solid or pasty in character, such as toothpowder, dental tablets, toothpaste or dental cream. Such compositions typically have a pH like that of a mouthwash. The vehicle of such solid or pasty oral preparations may contain polishing materials.

In compositions, such as mouthwashes and toothpastes, a surfactant is often present to promote foaming. The surfactants are nonionic.

Any suitable flavoring or sweetening material may also be employed.

The antibacterial compositions may be prepared by dispersing the vinyl copolymer in a vehicle which typically includes water.

For instance, an antibacterial mouthwash may be prepared by mixing an aqueous-humectant vehicle such as mixing ethanol, water, flavoring oil, nonionic surfactant and humectant with a vinyl copolymer. Additional water is added as desired.

A toothpaste may be prepared by forming a gel with water, humectant, gum or thickener such as hydroxyethyl cellulose, sweetener and adding thereto polishing agent, flavor, vinyl copolymer and additional water.

The following tests were made to determine the ability of the vinyl copolymer compositions to inhibit in vitro plaque formation by allowing plaque to form (for 48 hours at 37° C.) on the surfaces of conditioned glass rod substrates.

Glass rod substrates were chosen because of their similarity to human teeth in that the rods are negatively charged and are pervious. The following test was used in each of the following examples.

Plaque Accumulation Procedure

1. Substrate Preparation
   (a) Sterilize glass rod substrates in an autoclave.
   (b) Condition substrates by soaking in clarified human saliva for 1 hour at 37° C. The clarified human saliva was prepared by the following sequence:
   (1) having a human subject chew Parafilm TM, a parafin sold by American Can Company;
   (2) expectorate into chilled container;
   (3) collect and filter the expectorate through a milk filter;
   (4) centrifuge the filtrate 10,000 G/15 minutes (to remove bacteria) and decant off the liquid;
   (5) heat the liquid to 60° C. for 30 minutes (to kill enzymes);
   (6) centrifuge again 10,000 G/15 minutes and decant liquid; and
   (7) store the resulting clarified human saliva in the freezer.
   (c) Dip the substrates into 0.85% sterile NaCl solution for 1 minute at 37° C.
   d) Repeat step 1(c) two more times in fresh portions of NaCl solutions each time.

2. Culture Used

The culture was Streptococcus Mutans 6715-15 (rat organism) in a complex medium containing sucrose. Streptococcus Mutans is generally considered to be the most active bacterial organism involved in tooth decay. The culture was prepared by standard microbiological procedures.

3. Substrate Treatment
   (a) Dip substrates into an aqueous composition of the composition of the selected water-dispersible vinyl polymer.
   (b) Dip substrates into 0.85% NaCl for 1 minute at 37° C.
   (c) Repeat 3(b) two more times in fresh portions of NaCl solutions each time.

4. Plaque Growth
   (a) Suspend substrate, after treatment in 3, in the culture.
   (b) Incubate the substrates for 3 hours at 37° C. in a constant temperature chamber.
   (c) Repeat 3(a), 3(b) and 3(c).
   (d) Repeat 4(a) and 4(b)
   (e) Repeat 3(a), (b) and (c).
   (f) Repeat 4(a) and incubate overnight at 37° C.
   (g) Repeat 4(a)-4(f), inclusive using a fresh culture.

5. Plaque Assessment
   a) Dip substrates obtained from 4. into 0.85% NaCl for 1 minute at 37° C.
   (b) Repeat 5(a) two more times in fresh portions of NaCl solutions each time.
   (c) Harvest plaque by mechanical removal. Determine amount of plaque by determining absorbance spectrophotometrically at 700 nm. The NaCl-treated control consists of glass rod substrates that are subjected to the above plaque accumulation procedure excluding steps 3(a), (b) and (c).

EXAMPLE 4

Using the plaque accumulation protocol described above with glass rod substrates, Polymer 1, Table I, at 0.1% concentration was found to have a plaque accumulation of 3% (mean of 4 replicates) compared to a sodium chloride reference whose plaque accumulation was defined at 100%.

In a standard oral toxicity test conducted on rats this composition was shown to be practically nontoxic orally with an acute oral $LD_{50}$ value of greater than 6400 mg/kg body weight.

EXAMPLE 5

Using the plaque accumulation protocol described hereinbefore with glass rod substrates and a 0.1% concentration, Polymer 2, Table I was found to have a plaque accumulation of 12% compared to a sodium chloride reference whose plaque accumulation was defined at 100%.

EXAMPLE 6

Using the plaque accumulation protocol described above with glass rod substrates and a 0.1% concentration, Polymer 3, Table I was found to have a plaque accumulation of 38%.

EXAMPLE 7

Evaluation of Polymer 4

Using the plaque accumulation protocol described hereinbefore with glass rod substrates and a 0.1% concentration, polyer 4, Table I, was found to have a plaque accumulation of 4% compared to a sodium chloride reference whose plaque accumulation was defined as 100%.

Comparative Example 8

Using the plaque accumulation described hereinbefore, four vinyl polymers having recurring quaternary amine components were tested for antibacterial activity using 0.1% aqueous solutions of each polymer. These polymers are outside the scope of the present invention. The results are presented in Table II.

TABLE II

| | Plaque Accumulation |
|---|---|
| 1. Poly[N,N—dimethyl-N—dodecyl-N—(m- + p-vinylbenzyl)ammonium fluoride (60:40) -co-N,N,N—trimethyl-N—(m- + p-vinylbenzyl) ammonium fluoride (60:40)] (mole ratio 1.0:1.5) | 70.57% |
| 2. Poly[N,N,N—tri(n-propyl)-N—(m- + p-vinylbenzyl)ammonium fluoride] | 83.54% |
| 3. Poly[N,N,N—tri(n-butyl)-N—(m- + p-vinylbenzyl)ammonium fluoride] | 80.38% |
| 4. Poly[N—(2-hydroxyethy)-4-vinylpyridinium fluoride] | 72% |

These data show that not all vinyl polymers having quaternary nitrogen product groups will have acceptable antibacterial activity. Selection of those which do have significant antibacterial activity is unobvious.

Comparative Example 9

In vitro microelectrophoretic adsorption measurements were conducted to compare the effectiveness of (a) polymer 1, Table I and (b) chlorohexidine diacetate and cetyl pyridinium chloride in changing negatively charged hydroxy apatite to positively charged hydroxy apatite. Hydroxy apatite is the main inorganic constituent of human teeth. Chlorohexidine and cetyl pyrindinium are compounds used in oral anti-plaque dental compositions for humans. The experiments showed that polymer 1 changed the charge on hydroxy apatite from negative to positive at a concentration of 1.0 to $8.0 \times 10^{-6}$ g/ml. Chlorohexidine diacetate and cetyl pyridinium chloride required a concentration of $0.9. \times 10^{-4}$ and $3.0 \times 10^{-3}$ g.ml respectively. These measurements show that the polymers of the invention adhere to hydroxy apatite much more strongly than the smaller molecules of chlorohexidine diacetate and cetyl pyridinium chloride. The enhanced adsorption of polymer 1 compared to the latter two compounds is believed to also enhance the anti-plaque effectiveness of the polymers of this invention compared to smaller molecules.

The invention has been described in detail with particular reference to preferred embodiments thereof, but it will be understood that variations and modifications can be effected within the spirit and scope of the invention.

What is claimed is:

1. A water-dispersible vinyl copolymer comprising
   (a) from 15 to 90 mole percent of recurring polymerized vinyl monomer units having a quaternary nitrogen cationic group containing an alkyl substituent having 14 to 20 carbon atoms and
   (b) from 10 to 85 mole percent recurring polymerized vinyl monomer units having a quaternary nitrogen cationic group having one or more alkyl substituents containing less than 14 carbon atoms.

2. The copolymer of claim 1 comprising units having the structure

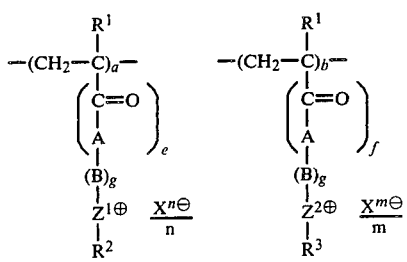

wherein each $R^1$ is independently hydrogen or methyl;

each A is independently —O— or —NH—;

each B is independently alkylene of about 1 to 20 carbon atoms, arylene of about 6 to 14 carbon atoms and arylenealkylene of about 7 to 15 carbon atoms;

$Z^1$ and $Z^2$ are each independently a quaternary nitrogen-containing group having the structure

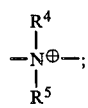

or a quaternary nitrogen containing group having the structure

wherein

G represents the carbon, hydrogen and hetero atoms necessary to complete a substituted or unsubstituted mono- or polycyclic nitrogen-containing cationic group having about 5 to 14 ring carbon and hetero atoms; or $Z^2$ taken together with $R^3$ represents a monovalent group having the structure

wherein G is as defined above;

$R^2$ is an alkyl group having 14 to 20 carbon atoms;

$R^3$, $R^4$ and $R^5$ are each independently an alkyl group of 1 to 4 carbon atoms;

$X^n/n$ and $X^m/m$ are independently mono- or multivalent acid anion in which n is 1 to 3 and m is 1 to 3;

a is 15 to 90 mole percent;

b is 10 to 85 mole percent; and e, f, g and h are each independently 0 or 1.

3. The polymer of claim 2 wherein:

each $R^1$ is independently hydrogen or methyl;

each A is —NH—;

each B is independently alkylene of about 1 to 3 carbon atoms, phenylene and phenylenemethylene;

$Z^1$ and $Z^2$ are each independently

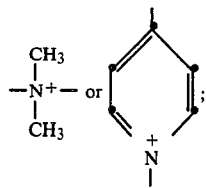

Z² together with R³ represents

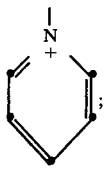

R² is an alkyl group having 16 to 18 carbon atoms;
X represents chloride;
R³ represents methyl;
a is 15 to 90 mole percent;
b is 10 to 85 mole percent; and
e, f, g and h are each independently 0 or 1.

4. The polymer of claim 3 selected from the group consisting of:
(a) poly[N-vinylbenzyl-N,N-dimethyl-N-octadecylammonium chloride-co-N-vinylbenzyl-N,N,N-trimethylammonium chloride];
(b) poly-N-vinylbenzyl-N,N-dimethyl-N-hexadecylammonium chloride-co-N-vinylbenzyl-N,N,N-trimethylammonium chloride-co-p-divinylbenzene];
(c) poly[N-vinylbenzyl-N,N-dimethyl-N-octadecylammonium chloride-co-N-vinylbenzyl-N,N,Ntrimethylammonium chloride-co-vinylbenzyl 9-anthrylmethyl ether];
(d) poly[N,N-dimethyl-N-(3-methacrylamidopropyl)-N-octadecylammonium chloride-co-N-(3-methacrylamidopropyl)-N,N,N-trimethylammonium chloride];
(e) poly(N-methyl-4-vinylpyridinium chloride-co-N-octadecyl-4-vinylpyridinium chloride); and
(f) poly[N-vinylbenzyl-N,N-dimethyl-N-octadecylammonium chloride-co-N-vinylbenzylpyridinium chloride-co-N-vinylbenzyl-N,N,N-trimethylammonium chloride].

5. The polymer of claim 3 selected from the group consisting of:
(a) poly[N-(m-+p-(vinylbenzyl)-N,N-dimethyl-N-octadecylammonium chloride (60:40) -co-N-(m-+p-vinylbenzyl)-N,N,N-trimethylammonium chloride (60:40)](mole ratio 1:1.5);
(b) poly-N-(m-+p-vinylbenzyl)-N,N-dimethyl-N-hexadecylammonium chloride (60:40) -co-N-(m-+p-vinylbenzyl)-N,N,N-trimethylammonium chloride (60:40) -co-p-divinylbenzene](molar ratio 87.75:9.75:2.5);
(c) poly[N-(m-+p-vinylbenzyl)-N,N-dimethyl-N-octadecylammonium chloride (60:40) -co-N-(m-+p-vinylbenzyl)-N,N,N-trimethylammonium chloride (60:40) -co-m-+p-vinylbenzyl 9-anthrylmethyl ether (60:40)](mole ratio 59:40:1);
(d) poly[N,N-dimethyl-N-(3-methacrylamidopropyl)-N-octadecylammonium chloride-co-N-(3-methacrylamidopropyl)-N,N,N-trimethylammonium chloride](mole ratio 1.0:1.5);
(e) poly(N-methyl-4-vinylpyridinium chloride-co-N-octadecyl-4-vinylpyridinium chloride) (mole ratio 2.0:1.0);
(f) poly[N-(m-+p-vinylbenzyl)-N,N-dimethyl-N-octadecylammonium chloride (60:40) -co-N-(m- +p-vinylbenzyl)-N,N,N-trimethylammonium chloride (60:40)](mole ratio 1:2.85);
(g) poly[N-(m-+p-vinylbenzyl)-N,N-dimethyl-N-octadecylammonium chloride (60:40) -co-N-(m-+p-vinylbenzyl)pyridinium chloride (60:40) -co-N-(m-+p-vinylbenzyl)-N,N,N-trimethylammonium chloride (60:40)](mole ratio 1.0:2.0:0.85).

6. An antibacterial composition comprising a carrier and a water-dispersible vinyl copolymer comprising
(a) from 15 to 90 mole percent of recurring polymerized vinyl monomer units having a quaternary nitrogen cationic group containing an alkyl substituent having 14 to 20 carbon atoms and
(b) from 10 to 85 mole percent recurring polymerized vinyl monomer units having a quaternary nitrogen cationic group having one or more alkyl substituents containing less than 14 carbon atoms.

7. The composition of claim 6 wherein the vinyl copolymer has the structure

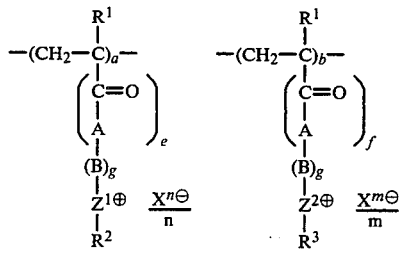

wherein
each R¹ is independently hydrogen or methyl;
each A is independently —O— or —NH—;
each B is independently alkylene of about 1 to 20 carbon atoms, arylene of about 6 to 14 carbon atoms and arylenealkylene of about 7 to 15 carbon atoms;
Z¹ and Z² are each independently a quaternary nitrogen-containing group having the structure

or a quaternary nitrogen containing group having the structure

wherein
G represents the carbon, hydrogen and hetero atoms necessary to complete a substituted or unsubstituted mono- or polycyclic nitrogen-containing cationic group having about 5 to 14 ring carbon and hetero atoms; or
Z² taken together with R³ represents a monovalent group having the structure

wherein G is as defined above;
R² is an alkyl group having 14 to 20 carbon atoms;
R³, R⁴ and R⁵ are each independently an alkyl group of 1 to 4 carbon atoms;
$X^n/$ n and $X^m/$m are independently mono- or multivalent acid anion in which n is 1 to 3 and m is 1 to 3;
a is 15 to 90 mole percent;
b is 10 to 85 mole percent; and
e, f, g and h are each independently 0 or 1.

8. The composition of claim 7 wherein:
each R¹ is independently hydrogen or methyl;
each A is —NH—;
each B is independently alkylene of about 1 to 3 carbon atoms, phenylene and phenylenemethylene;
Z¹ and Z² are each independently

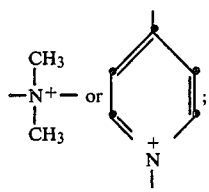

Z² together with R³ represents

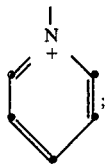

R² is an alkyl group having 16 to 18 carbon atoms;
X represents chloride;
R³ represents methyl;
a is 15 to 90 mole percent;
b is 10 to 85 mole percent; and
e, f, g and h are each independently 0 or 1.

9. The composition of claim 8 wherein the polymer is selected from the group consisting of:
(a) poly[N-vinylbenzyl-N,N-dimethyl-N-octadecylammonium chloride-co-N-vinylbenzyl-N,N,Ntrimethylammonium chloride];
(b) poly-N-vinylbenzyl-N,N-dimethyl-N-hexadecylammonium chloride-co-N-vinylbenzyl-N,N,N-trimethylammonium chloride-co-p-divinylbenzene];
(c) poly[N-vinylbenzyl-N,N-dimethyl-N-octadecylammonium chloride-co-N-vinylbenzyl-N,N,N-trimethylammonium chloride-co-vinylbenzyl 9-anthrylmethyl ether];
(d) poly[N,N-dimethyl-N-(3-methacrylamidopropyl)-N-octadecylammonium chloride-co-N-(3-methacrylamidopropyl)-N,N,N-trimethylammonium chloride];
(e) poly(N-methyl-4-vinylpyridinium chloride-co-N-octadecyl-4-vinylpyridinium chloride); and
(f) poly[N-vinylbenzyl-N,N-dimethyl-N-octadecylammonium chloride-co-N-vinylbenzylpyridinium chloride-co-N-vinylbenzyl-N,N,N-trimethylammonium chloride].

10. The composition of claim 9 wherein the vinyl polymer is selected from the group consisting of:
(a) poly[N-(m-+p-(vinylbenzyl)-N,N-dimethyl-N-octadecylammonium chloride (60:40) -co-N-(m-+p-vinylbenzyl)-N,N,N-trimethylammonium chloride (60:40)](mole ratio 1:1.5);
(b) poly-N-(m- +p-vinylbenzyl)-N,N-dimethyl-N-hexadecylammonium chloride (60:40) -co-N-(m-+p-vinylbenzyl)-N,N,N-trimethylammonium chloride (60:40) -co-p-divinylbenzene](molar ratio 87.75:9.75:2.5);
(c) poly[N-(m-+p-vinylbenzyl)-N,N-dimethyl-N-octadecylammonium chloride (60:40) -co-N-(m-+p-vinylbenzyl)-N,N,N-trimethylammonium chloride (60:40) -co-p-+p-vinylbenzyl 9-anthrylmethyl ether (60:40)](mole ratio 59:40:1);
(d) poly[N,N-dimethyl-N-(3-methacrylamidopropyl)-N-octadecylammonium chloride-co-N-(3-methacrylamidopropyl)-N,N,N-trimethylammonium chloride](mole ratio 1.0:1.5);
(e) poly(N-methyl-4-vinylpyridinium chloride-co-N-octadecyl-4-vinylpyridinium chloride) (mole ratio 2.0:1.0);
(f) poly[N-(m-+p-vinylbenzyl)-N,N-dimethyl-N-octadecylammonium chloride (60:40) -co-N-(m-+p-vinylbenzyl)-N,N,N-trimethylammonium chloride (60:40)](mole ratio 1:2.85);
(g) poly[N-(m- +p-vinylbenzyl)-N,N-dimethyl-N-octadecylammonium chloride (60:40) -co-N-(m-+p-vinylbenzyl)pyridinium chloride (60:40) -co-N-(m-+p-vinylbenzyl)-N,N,N-trimethylammonium chloride (60:40)](mole ratio 1.0:2.0:0.85).

11. The composition of claim 7, 8, 9 or 10 wherein the carrier is selected from the group consisting of water, a water-alcohol mixture, toothpowder and toothpaste.

12. The composition of claim 7, 8, 9 or 10 wherein the concentration of the vinyl polymer in the carrier is 0.001 to 10 weight percent.

13. A method for inhibiting the growth of plaque on human teeth comprising the step of treating the teeth with a composition comprising a carrier and a water-dispersible vinyl polymer of claim 7, 8, 9 or 10.

14. The composition of claim 7, 8, 9 or 10 in the form of an oral mouthwash, toothpowder or toothpaste.

15. The composition of claim 7, 8, 9 or 10 wherein the polymer is a microgel comprising polymerized recurring crosslinking units.

16. The composition of claim 6, 7, 8, 9 or 10 wherein the polymer is a microgel comprising polymerized recurring units derived from divinyl benzene.

* * * * *

UNITED STATES PATENT AND TRADEMARK OFFICE
CERTIFICATE OF CORRECTION

PATENT NO. : 4,621,120  
DATED : November 4, 1986  
INVENTOR(S) : Kenneth R. Hollister Page 1 of 2

It is certified that error appears in the above-identified patent and that said Letters Patent is hereby corrected as shown below:

Column 2, line 1;  
Column 12, line 1 and  
Column 14, line 29 the part of the structure reading "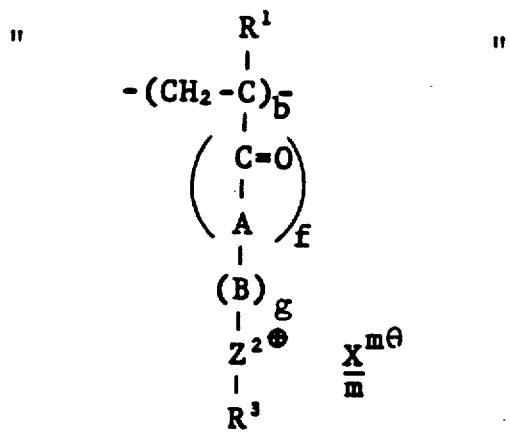"

UNITED STATES PATENT AND TRADEMARK OFFICE
CERTIFICATE OF CORRECTION

PATENT NO. : 4,621,120

DATED : November 4, 1986

INVENTOR(S) : Kenneth R. Hollister

It is certified that error appears in the above-identified patent and that said Letters Patent is hereby corrected as shown below:

should read

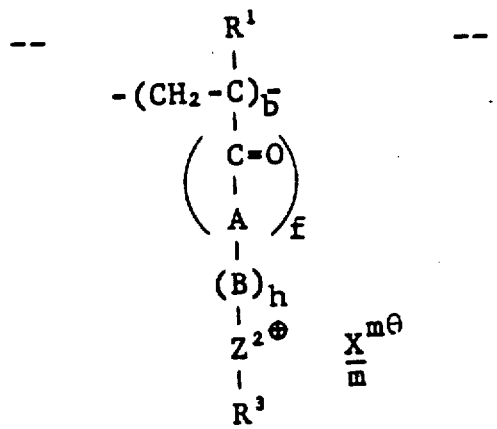

Signed and Sealed this

Twenty-seventh Day of January, 1987

*Attest:*

DONALD J. QUIGG

*Attesting Officer*    *Commissioner of Patents and Trademarks*